(12) United States Patent
Bryant et al.

(10) Patent No.: US 10,349,996 B2
(45) Date of Patent: Jul. 16, 2019

(54) APPARATUS, SYSTEM, AND METHOD FOR SECURING A TENSIONED CABLE THROUGH OR AROUND BONE

(71) Applicant: Cable Fix LLC, Hernando, MS (US)

(72) Inventors: Carey Bryant, Hernando, MS (US);
Mark Brinker, Houston, TX (US);
William Ricci, Richmond Heights, MO (US)

(73) Assignee: CABLE FIX LLC, Hernando, MS (US)

( * ) Notice: Subject to any disclaimer, the term of this patent is extended or adjusted under 35 U.S.C. 154(b) by 796 days.

(21) Appl. No.: 14/961,506

(22) Filed: Dec. 7, 2015

(65) Prior Publication Data
US 2017/0156779 A1    Jun. 8, 2017

(51) Int. Cl.
| A61B 17/56 | (2006.01) |
| A61B 17/58 | (2006.01) |
| A61B 17/82 | (2006.01) |
| A61F 2/30 | (2006.01) |
| A61B 17/88 | (2006.01) |

(52) U.S. Cl.
CPC .......... *A61B 17/8869* (2013.01); *A61B 17/82* (2013.01); *A61B 17/8863* (2013.01)

(58) Field of Classification Search
CPC combination set(s) only.
See application file for complete search history.

(56) References Cited

U.S. PATENT DOCUMENTS

| 479,938 | A | 8/1892 | Fredlihp |
| 899,612 | A | 9/1908 | Phillips |
| 2,634,474 | A | 4/1953 | Grayson |
| 3,166,072 | A | 1/1965 | Sullivan, Jr. |
| 3,952,377 | A | 4/1976 | Morell |
| 4,060,089 | A | 11/1977 | Noiles |
| 4,127,119 | A | 11/1978 | Kronner |
| 4,145,075 | A | 3/1979 | Holzmann |
| 4,250,348 | A | 2/1981 | Kitagawa |
| 4,358,079 | A | 11/1982 | Navarro |
| 4,455,717 | A | 6/1984 | Gray |
| 4,532,927 | A | 8/1985 | Miksza, Jr. |
| 4,534,350 | A | 8/1985 | Golden et al. |
| 4,534,352 | A | 8/1985 | Korthoff |
| 4,548,202 | A | 10/1985 | Duncan |
| 4,573,469 | A | 3/1986 | Golden et al. |
| 4,610,250 | A | 9/1986 | Green |
| 4,754,758 | A | 7/1988 | Lehmann |
| 4,932,960 | A | 6/1990 | Green |
| 5,350,204 | A | 9/1994 | Henniger |
| 5,358,510 | A | 10/1994 | Luscombe et al. |
| 5,378,027 | A | 1/1995 | Gehring |
| 5,383,905 | A | 1/1995 | Golds |
| 5,405,172 | A | 4/1995 | Mullen, Jr. |

(Continued)

OTHER PUBLICATIONS

Office Action for U.S. Appl. No. 15/709,436 dated May 17, 2018.

*Primary Examiner* — Sameh R Boles
(74) *Attorney, Agent, or Firm* — Kunzler Bean & Adamson (57) ABSTRACT

An apparatus for crimping a cable, the apparatus including a crimp body, an elongate shaft, a neck coupling and interposed between the crimp body and the elongate shaft, and a central passage extending through the crimp body, neck, and elongate shaft. The cross-sectional dimension of the central passage is at least large enough to receive the cable.

14 Claims, 7 Drawing Sheets

(56) References Cited

U.S. PATENT DOCUMENTS

| | | |
|---|---|---|
| 5,405,359 A | 4/1995 | Pierce |
| 5,478,353 A | 12/1995 | Yoon |
| 5,507,754 A | 4/1996 | Green |
| 5,620,452 A | 4/1997 | Yoon |
| 5,665,109 A | 9/1997 | Yoon |
| 5,702,397 A | 12/1997 | Goble |
| 5,725,529 A | 3/1998 | Nicholson |
| 5,797,932 A | 8/1998 | Min et al. |
| 5,872,335 A | 2/1999 | Mullen, Jr. |
| 5,908,421 A | 6/1999 | Berger |
| 5,957,953 A | 9/1999 | DiPoto |
| 6,056,773 A | 5/2000 | Bonutti |
| 6,086,608 A | 7/2000 | Ek |
| 6,260,241 B1 | 7/2001 | Brennan |
| 6,276,032 B1 | 8/2001 | Nortman et al. |
| 6,306,159 B1 | 10/2001 | Schwartz |
| 6,368,326 B1 | 4/2002 | Dakin |
| 6,488,317 B1 | 12/2002 | Daoud |
| 6,585,730 B1 | 7/2003 | Foerster |
| 6,648,903 B1 | 11/2003 | Pierson |
| 6,712,830 B2 | 3/2004 | Esplin |
| 6,966,919 B2 | 11/2005 | Sixto et al. |
| 7,033,378 B2 | 4/2006 | Smith et al. |
| 7,094,251 B2 | 8/2006 | Bonutti et al. |
| 7,172,595 B1 | 2/2007 | Goble |
| 7,491,217 B1 | 2/2009 | Hendren |
| 7,625,387 B2 | 12/2009 | Wixey |
| 7,674,276 B2 | 3/2010 | Stone |
| 7,678,122 B2 | 3/2010 | Kortenbach et al. |
| 7,717,916 B2 | 5/2010 | Hajianpour |
| 7,854,750 B2 | 12/2010 | Bonutti et al. |
| 7,985,241 B2 | 7/2011 | Smith et al. |
| 8,080,020 B2 | 12/2011 | Kortenbach et al. |
| 8,114,100 B2 | 2/2012 | Smith et al. |
| 8,162,977 B2 | 4/2012 | Bonutti et al. |
| 8,419,733 B2 | 4/2013 | Hajianpour |
| 8,454,628 B2 | 6/2013 | Smith et al. |
| 8,613,750 B2 | 12/2013 | Smith et al. |
| 9,039,596 B2 | 5/2015 | Sater |
| 9,220,503 B2 | 12/2015 | Ranchod |
| 9,265,543 B2 | 2/2016 | Gephart |
| 9,375,242 B2 | 6/2016 | Worcel |
| 9,439,698 B2 | 9/2016 | Songer |
| 9,788,827 B2 | 10/2017 | Miksza et al. |
| 9,788,875 B2 | 10/2017 | Dell'oca |
| 9,788,877 B2 | 10/2017 | Dell'oca |
| 2001/0008971 A1 | 7/2001 | Schwartz |
| 2001/0025181 A1 | 9/2001 | Freedlan |
| 2001/0051815 A1 | 12/2001 | Esplin |
| 2002/0029044 A1 | 3/2002 | Monassevitch et al. |
| 2002/0116013 A1 | 8/2002 | Gleason |
| 2002/0128684 A1 | 9/2002 | Foerster |
| 2002/0133179 A1 | 9/2002 | McDevitt |
| 2003/0023241 A1 | 1/2003 | Drewry |
| 2003/0225456 A1 | 12/2003 | Ek |
| 2004/0044366 A1 | 3/2004 | Bonutti et al. |
| 2004/0059349 A1 | 3/2004 | Sixto et al. |
| 2004/0059354 A1 | 3/2004 | Smith et al. |
| 2004/0059358 A1 | 3/2004 | Kortenbach et al. |
| 2004/0098050 A1 | 5/2004 | Foerster |
| 2004/0127907 A1 | 7/2004 | Dakin |
| 2006/0195104 A1 | 8/2006 | Schlafli |
| 2007/0010817 A1 | 1/2007 | de Conninck |
| 2007/0032825 A1 | 2/2007 | Bonutti et al. |
| 2007/0255317 A1 | 11/2007 | Fanton |
| 2008/0023012 A1 | 1/2008 | Dineen |
| 2008/0046007 A1 | 2/2008 | Schwemberger et al. |
| 2008/0046008 A1 | 2/2008 | Smith et al. |
| 2008/0097430 A1 | 4/2008 | Berstein et al. |
| 2008/0108897 A1 | 5/2008 | Bonutti et al. |
| 2008/0140095 A1 | 6/2008 | Smith et al. |
| 2008/0147116 A1 | 6/2008 | Smith et al. |
| 2008/0147126 A1 | 6/2008 | Tipirneni |
| 2008/0147127 A1 | 6/2008 | Tipirneni |
| 2008/0149685 A1 | 6/2008 | Smith et al. |
| 2008/0275469 A1 | 11/2008 | Fanton |
| 2008/0319478 A1 | 12/2008 | Foerster |
| 2009/0131990 A1 | 5/2009 | Tipirneni |
| 2009/0149883 A1 | 6/2009 | Brunsvold |
| 2009/0171357 A1 | 7/2009 | Justin |
| 2009/0248068 A1 | 10/2009 | Lombardo |
| 2009/0254129 A1 | 10/2009 | Tipirneni |
| 2009/0306718 A1 | 12/2009 | Tipirneni |
| 2009/0312794 A1 | 12/2009 | Nason |
| 2010/0049213 A1 | 2/2010 | Serina |
| 2010/0179568 A1 | 7/2010 | Kortenbach et al. |
| 2010/0256612 A1 | 10/2010 | Dell'Oca |
| 2010/0292733 A1 | 11/2010 | Hendricksen |
| 2010/0298893 A1 | 11/2010 | Stucki |
| 2010/0312292 A1 | 12/2010 | Tipirneni |
| 2010/0318137 A1 | 12/2010 | Stucki |
| 2011/0034925 A1 | 2/2011 | Tipirneni |
| 2011/0040307 A1 | 2/2011 | Ranchod |
| 2011/0092993 A1 | 4/2011 | Jacobs |
| 2011/0201877 A1 | 8/2011 | Sater |
| 2011/0224676 A1 | 9/2011 | Dell'oca |
| 2011/0295252 A1 | 12/2011 | Tipirneni |
| 2012/0065638 A1* | 3/2012 | Moore ................ A61B 17/72 606/62 |
| 2012/0078300 A1 | 3/2012 | Mayer |
| 2012/0130374 A1 | 5/2012 | Bouduban et al. |
| 2012/0143247 A1 | 6/2012 | Smith et al. |
| 2012/0215224 A1 | 8/2012 | Songer |
| 2013/0123841 A1 | 5/2013 | Lyon |
| 2013/0184708 A1 | 7/2013 | Robinson |
| 2013/0331896 A1 | 12/2013 | Holt |
| 2013/0331897 A1 | 12/2013 | Holt |
| 2014/0025111 A1 | 1/2014 | Bonutti |
| 2014/0107710 A1 | 4/2014 | Forderer |
| 2014/0194907 A1 | 7/2014 | Bonutti |
| 2014/0316461 A1 | 10/2014 | Skiar |
| 2015/0032154 A1 | 1/2015 | Kaplan |
| 2015/0057706 A1 | 2/2015 | Fallin |
| 2015/0073475 A1 | 3/2015 | Schaller |
| 2016/0038186 A1 | 2/2016 | Herzog |
| 2016/0081686 A1 | 3/2016 | Miksza et al. |
| 2016/0100835 A1 | 4/2016 | Linder et al. |
| 2016/0346023 A1 | 12/2016 | Bouduban et al. |
| 2017/0035552 A1 | 2/2017 | Fallin |
| 2017/0065319 A1 | 3/2017 | Oldakowska |
| 2017/0128114 A1 | 5/2017 | Songer |
| 2017/0156738 A1 | 6/2017 | Ricci et al. |
| 2017/0156771 A1 | 6/2017 | Brinker |
| 2017/0156772 A1 | 6/2017 | Brinker et al. |
| 2017/0156774 A1 | 6/2017 | Bryant et al. |
| 2017/0156775 A1 | 6/2017 | Bryant |
| 2017/0156779 A1 | 6/2017 | Bryant |
| 2017/0156847 A1 | 6/2017 | Ricci et al. |
| 2017/0258572 A1 | 9/2017 | Gordon |
| 2017/0265854 A1 | 9/2017 | Heaven |
| 2018/0049735 A1 | 2/2018 | Nguyen |
| 2018/0055550 A1 | 3/2018 | Bryant et al. |
| 2018/0070933 A1 | 3/2018 | Walters |
| 2019/0083155 A1 | 3/2019 | Bryant et al. |

* cited by examiner

APPARATUS, SYSTEM, AND METHOD FOR SECURING A TENSIONED CABLE THROUGH OR AROUND BONE

FIELD

The subject matter of the present disclosure relates generally to securing a tensioned cable through or around bone. More specifically, the present disclosure relates to crimping a crimp body to a tensioned cable that extends through or around bone.

BACKGROUND

Various medical procedures utilize cables or conventional sutures to secure damaged skeletal tissue or soft tissue. Tissues, such as bones or soft-tissues, that have been fragmented, fractured, broken, torn, pulled, stretched, or otherwise damaged need to be set and held in specific orientations in order to properly heal. Cables or conventional sutures may be useful for securing/attaching torn tissue back together or for facilitating holding bone fragments in place. For example, cerclage cables or conventional sutures can be wrapped around or lie adjacent to bone for fracture reduction, fracture fixation, and crack propagation prevention. However, conventional tools and procedures for utilizing cables or conventional sutures in medical surgeries are generally time-consuming, complex, and usually involve multiple in-situ steps that are difficult to perform.

SUMMARY

From the foregoing discussion, it should be apparent that a need exists for an apparatus, system, and method for fracture reduction, fracture fixation, and crack propagation prevention that overcome the limitations of conventional medical tools and procedures. Beneficially, such an apparatus, system, and method would improve the ease, efficiency, and effectiveness of medical procedures for fracture reduction, fracture fixation, and crack propagation prevention.

The subject matter of the present application has been developed in response to the present state of the art, and in particular, in response to the problems and needs in the art that have not yet been fully solved by currently available medical tools and procedures. For example, the ease, efficiency, and effectiveness of fracture reduction, fracture fixation, and crack propagation prevention could be improved by tensioning and securing a cable through bone to reduce and/or secure a fracture. Accordingly, the present disclosure has been developed to provide an apparatus for tensioning a cable and securing the cable through bone, and its related systems and methods, that overcome many or all of the above-discussed shortcomings in the art.

Disclosed herein is one embodiment of an apparatus for securing a tensioned cable through bone. The apparatus includes a crimp body, an elongate shaft, a neck coupling and interposed between the crimp body and the elongate shaft, and a central passage extending through the crimp body, neck, and elongate shaft. The cross-sectional dimension of the central passage is at least large enough to receive the cable.

In one implementation, at least two of the crimp body, the elongate shaft, and the neck are integrated together to form a one-piece monolithic construction. In another implementation, the central passage is continuous through the crimp body, elongate shaft, and neck such that the cable is concurrently positionable within the crimp body, elongate shaft, and neck via the central passage. In such an embodiment, when the cable is positioned in the central passage within the crimp body, the crimp body is collapsible about the cable to crimp or lock the cable.

According to another implementation, a locking mechanism is disposed within the central passage of the elongate shaft. The locking mechanism is configured to lock the cable extending through the central passage, thereby maintaining any tension imparted to the cable. The locking mechanism may be a collet member translationally movable within the central passage of the elongate shaft. The collet member may have a central channel that extends through a plurality of prongs concentric with the central passage. The plurality of prongs of the collet member are configured to engage an interior surface of the central passage of the elongate shaft and compress inwardly towards the central channel to clamp around and lock the cable positioned in the central channel as the collet member translationally moves within the central passage of the elongate shaft.

In one implementation, the plurality of prongs of the collet member and the interior surface of the central passage of the elongate shaft converge in a direction extending from the elongate shaft to the crimp body. In another implementation, the collet member has external threads threadably engageable with conforming internal threads disposed in the central passage of the elongate shaft. In such an implementation, relative rotation between the collet member and the elongate shaft causes the collet member to translationally move within the central passage of the elongate shaft.

In another implementation, the elongate shaft has one or more pass-through apertures extending through one or more walls of the elongate shaft in a direction substantially perpendicular to a central axis of the elongate shaft. These pass-through apertures are configured to receive a tool for inducing relative rotation between the elongate shaft and the collet member. In one implementation, the collet member has a proximal-end portion that has a non-circular outer periphery. The non-circular outer periphery is mateable with a rotational tool for inducing relative rotation between the elongate shaft and the collet member.

In one implementation, a maximum cross-sectional dimension of the crimp body is larger than a maximum cross-sectional dimension of the neck. In another implementation, a maximum cross-sectional dimension of the elongate shaft is larger than the maximum cross-sectional dimension of the crimp body. The neck may be constructed from a material that is cut-able by a hand tool. In another implementation, the apparatus includes a washer coupled to the crimp body, such that the crimp body is interposed between the washer and the neck. In one implementation, at least two of the washer, the crimp body, the neck, and the elongate shaft are integrated together to form a one-piece monolithic construction. In one implementation, a cable is pre-attached to the washer.

Also disclosed herein is one embodiment of an apparatus for securing a tensioned cable through bone. The apparatus includes a crimp body collapsible about a cable to crimp or lock the cable, an elongate shaft, a neck coupling and interposed between the crimp body and the elongate shaft, and a central passage extending continuously through the crimp body, neck, and elongate shaft. The central passage is sized to receive the cable such that the cable is concurrently positionable within the crimp body, elongate shaft, and neck via the central passage. The central passage also has internal threads. A collet member disposed within and translationally movable within the central passage of the elongate shaft is configured to clamp around and lock the cable extending through the central passage at a measurable and adjustable tension. The collet member has external threads threadably conforming and engageable with the internal threads disposed in the central passage of the elongate shaft.

In such an embodiment, the crimp body, the elongate shaft, and the neck are integrated to form a one-piece monolithic construction. Also, the collet member has a central channel extending through a plurality of prongs concentric with the central passage. Further, the plurality of prongs of the collet member are configured to engage an interior surface of the central passage of the elongate shaft and compress inwardly towards the central channel to lock a cable positioned in the central channel as the collet member translationally moves within the central passage of the elongate shaft.

Also disclosed herein is one embodiment of a method for securing a tensioned cable through bone. The method includes passing a cable through a central passage extending continuously through a crimp body, an elongate shaft, and a neck. The neck is non-movably coupled to and interposed between the crimp body and the elongate shaft. Still further, the method includes moving the elongate shaft to position the crimp body in a desired position relative to a hole in a bone and tensioning the cable to a measurable and adjustable tension, to cause a measurable and adjustable compression of the bone by the cable. After the crimp body is in the desired position and once the cable is tensioned to the measurable and adjustable tension, the method includes crimping the crimp body about the cable and then cutting the neck to detach the crimp body from the elongate shaft.

In certain implementations, the method further includes passing the cable through a central channel of a collet member disposed within and concentric with the central passage of the elongate shaft. The method may include compressing the central channel of the collet member to lock the cable at the measurable and adjustable tension.

According to one implementation, cutting the neck includes concurrently cutting the cable positioned within the central passage of the neck. In another implementation, compressing the central channel of the collet member includes translationally moving the collet member within the central passage of the elongate shaft to engage a plurality of prongs of the collet member with an interior surface of the central passage. The collet member may have external threads threadably engageable with conforming internal threads disposed in the central passage of the elongate shaft. Relative rotation between the collet member and the elongate shaft causes the collet member to translationally move within the central passage of the elongate shaft. In another implementation, tensioning the cable includes attaching a tensioner device to the elongate shaft and actuating the tensioner device to impart the measurable and adjustable tension to the cable.

In certain implementations of the method, the desired position is relative to a hole in the bone, and the method further includes passing the cable through the hole before tensioning the cable to the measurable and adjustable tension. According to some implementations, the method further includes wrapping the cable around the bone before tensioning the cable to the measurable and adjustable tension. The cable can be fixedly secured relative to the crimp body before passing the cable through the central passage. In yet some implementations, crimping the crimp body about the cable and cutting the neck are performed in a single action.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure.

Illustrated in FIGS. 1-9 are several representative embodiments of an apparatus 100 for attaching a crimp body 105 to a cable. As described herein, the apparatus for attaching the crimp body to the cable provides various advantages and benefits over other medical tools and procedures. However, the recited advantages are not meant to be limiting in any way, as one skilled in the art will appreciate that other advantages may also be realized upon practicing the present disclosure.

Figure 1:
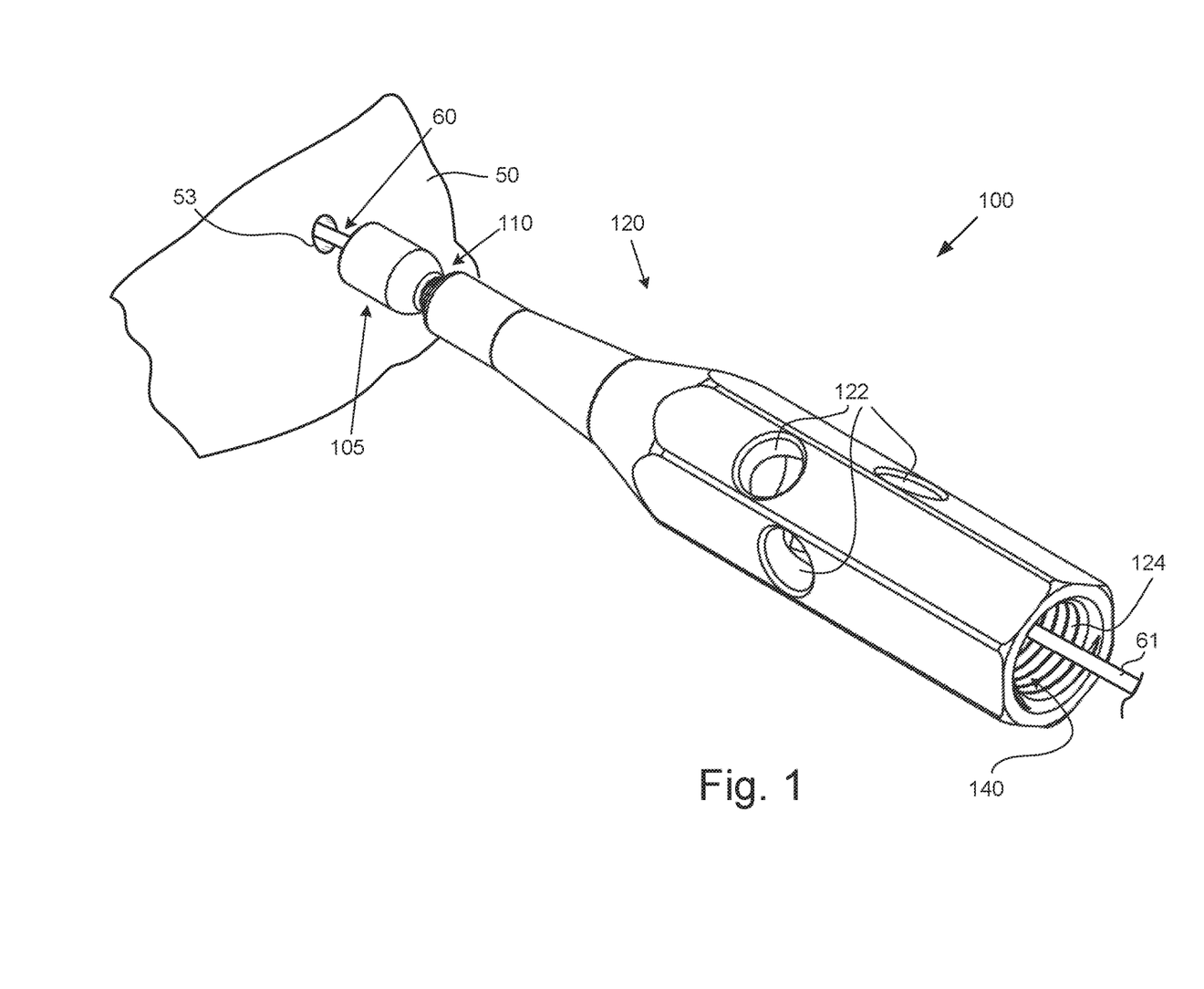
FIG. 1 is side perspective view of an apparatus for attaching a crimp body to a cable, with the apparatus including a crimp body, a neck, and an elongate shaft, according to one embodiment.

FIG. 1 is a perspective view of one embodiment of the apparatus 100 for attaching the crimp body 105 to a cable. The apparatus 100 includes the crimp body 105, a neck 110, and an elongate shaft 120. The neck 110 is interposed between the crimp body 105 and the elongate shaft 120. A continuous central passage 140 extends through the crimp body 105, neck 110, and elongate shaft 120 such that the cable 60 is concurrently positionable within the crimp body 105, neck 110, and elongate shaft 120 via the central passage 140. In one embodiment, at least two of the crimp body 105, the neck 110, and the elongate shaft 120 are integrated together to form a one-piece monolithic construction. For example, the crimp body 105 and the neck 110 may be formed together as one-piece monolithic construction that is separately coupled to the elongate shaft 120. Alternatively, as an example, the crimp body 105, the neck 110, and the elongate shaft 120 may all be formed together as a one-piece monolithic construction.

As defined herein, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 60 may be passed through a pass-through hole (e.g., a tunnel, passage, or passageway) in a bone and may be tensioned to a measurable and adjustable tension in order to facilitate the reduction and fixation of fractures or to otherwise facilitate the repair of dislocations or soft-tissue damage. In other words, the cable 60 is not a conventional suture or conventional thread material, since such materials are incapable of, or at least not well-suited for, maintaining a measurable and adjustable tension. Thus, the term "cable" can refer to a flexible, yet substantially non-stretchable, elongate cord-like element that can be tensioned to a measurable and adjustable tension. Because the cable 60 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 60 to be tensioned to a measurable and adjustable tension improves the reliability and reproducibility of surgical procedures when compared with other medical procedures that do not utilize cables. The cable 60 may be made from any one of various materials. For example, in specific implementations, the cable 60 is made from metal, such as stainless steel, titanium, or other metal.

Generally, the apparatus 100 enables a practitioner (e.g., a surgeon or other medical professional) to feed a cable 60 already extending from a hole 53 in a bone 50 through the central passage 140 of the apparatus 100 (i.e., the cable 60 is passed through the crimp body 105, the neck 110, and the elongate shaft 120). The practitioner then positions the crimp body 105 adjacent the bone, proximate the opening of the hole 53 in the bone 50, and tensions the cable 60 extending through central passage 140 of the apparatus 100 (i.e., the cable extends through the crimp body 105, the neck 110, and the elongate shaft 120). As described in greater detail below, the cable 60 may be tensioned manually by hand (e.g., pulling on a portion 61 of the cable 60 protruding from back side of the elongate shaft 120) or a tensioner device may be employed to exert a specified tension on the cable. In order for the cable to be tensioned, the opposing end of the cable must be anchored or securely retained. In one embodiment, the cable 60 may be coupled to a bone anchor that has been installed in a bone or on the surface of a bone. In another embodiment, the opposing end of the cable 60 has an attached crimp body or some other type of retainer feature that is engageable with the opposing surface of the bone proximate the opposite opening of the hole 53, thus preventing the cable from sliding through the hole in the bone and thereby ensuring that the cable holds tension.

Figure 9:
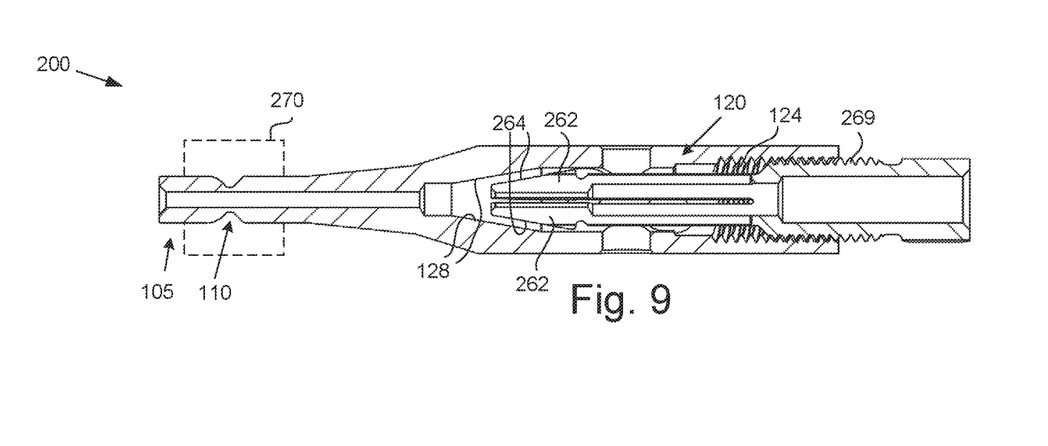
FIG. 9 is a cross-sectional side view of the apparatus of FIG. 4, according to one embodiment.

With the cable tensioned and the crimp body 105 positioned adjacent the bone 50, proximate the opening of the hole 53 in the bone 50, the practitioner can crimp the crimp body 105 to the cable 60, detach the crimp body 105 from the elongate shaft 120 by cutting the apparatus 100 at the neck 110, and cut the cable 60. According to one embodiment, crimping the crimp body 105 is performed first, but the two steps of cutting the neck 110 and cutting the cable 60 may be performed concurrently or sequentially. For example, a cutting tool may cut both the neck 110 and the cable 60 extending through the neck 110 in a single cutting action. In another embodiment, as shown in FIG. 9, a single tool 270 may be used to both crimp, the crimp body 105, and cut, the neck 110 and cable, in a single action. Moreover, in some implementations, the tool 270 may fit over at least a portion of the apparatus and/or be coaxial with the apparatus.

Although a single tool 270 is shown in FIG. 9, it is recognized that separate tools can be used. For example a first tool may be used to crimp the crimp body and a second tool may be used to cut the cable. However, in such an embodiment, the crimping would need to still occur before cutting the cable to avoid losing the tension in the cable. Since the cross-sectional dimension of the crimp body 105 is larger than the diameter of the hole 53 in the bone 50, after the cable 60 is cut the portion of the cable extending through the hole 53 in the bone 50 holds the tension since the crimp body 105 prevents the cable 60 from withdrawing into the hole 53 in the bone 50.

Although the depiction in FIG. 1 shows the crimp body 105 positioned a distance away from the opening of the hole 53 in the bone 50, in one embodiment the crimp body 105 is positioned in direct contact with the surface of the bone 50 surrounding the opening of the hole 53, thereby preventing any slack (e.g., loss of tension) in the cable 60 upon cutting the cable 60. In another embodiment, the crimp body 4105 is shaped and formed to nestably engage the cable-engaging surface of the cable washers described above (e.g., the cable-engaging surface 3110 of the washer 3100 in shown in FIG. 21A) in order to maintain tension in the cable 4060.

The apparatus has advantages over conventional tools and procedures. For example, the elongate shaft 120 provides a way for the practitioner to easily position the crimp body 105 into direct contact with the bone 50 without requiring the practitioner's hands to be inserted into the surgical area to hold a traditional crimp ball/feature in place. Further, a tensioner device may be mounted to the elongate shaft 120, thus allowing the tensioner device to be removed a distance away from the surgical tissue. Additional details relating to the method of using the apparatus, as well as details regarding additional components of the apparatus, are included below with reference to the remaining figures.

According to the embodiment shown in FIG. 1, the outer-periphery of the elongate shaft 120 is non-circular and the elongate shaft 120 has internal threads 124 and one or more pass-through apertures 122. The internal threads 124 and the pass-through apertures 122 are optional in certain implementations. Nevertheless, the internal threads 124 and pass-through apertures 122 are shown in FIGS. 1-3 in order to clearly disclose an alternative embodiment that is described below with reference to FIGS. 4-9.

Figure 2:
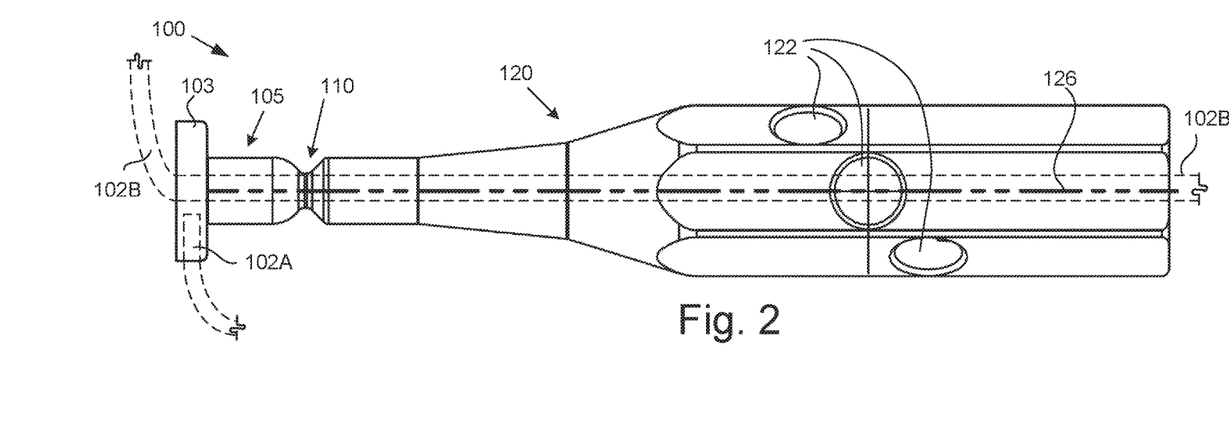
FIG. 2 is a side view of the apparatus of FIG. 1, but with a washer disposed adjacent the crimp body, according to one embodiment.
Figure 3:
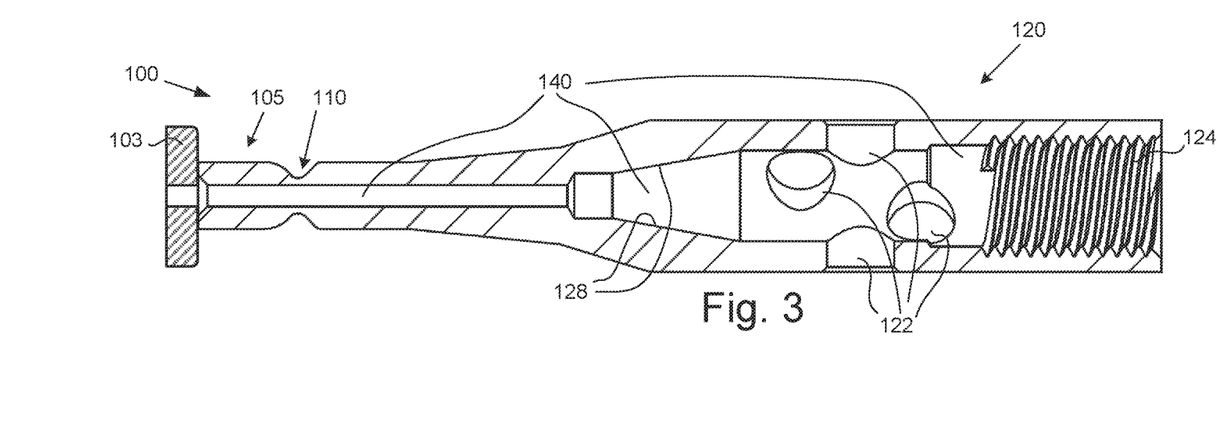
FIG. 3 is a cross-sectional side view of the apparatus of FIG. 2, according to one embodiment.

As shown in the embodiment depicted in FIGS. 1-3, a maximum cross-sectional dimension of the crimp body 105 is larger than a maximum cross-sectional dimension of the neck 110 and a maximum cross-sectional dimension of the elongate shaft 120 is larger than the maximum cross-sectional dimension of the crimp body 105. The neck 110 may be configured to have a small cross-sectional dimension to allow the neck 110 to be easily cut. Also, the elongate shaft 120 may have a comparatively larger cross-sectional dimension to allow the practitioner to easily grasp the apparatus 100 or to allow room for a locking mechanism to be positioned within the central passage 140 of the elongate shaft 120. In an alternative embodiment, the apparatus may have a substantially uniform cross-sectional dimension along its length. The locking mechanism may be configured to lock the cable extending through the central passage 140, thus preventing the cable 60 from moving through the central passage 140 and also holding any tension that may have been imparted to the cable 60. In one embodiment, a set screw threadably engages with the elongate shaft and can be rotated into contact with the cable 60 to lock the cable 60 in place relative to the apparatus 100 in order to retain any tension imparted to the cable 60. In such an embodiment, the set screw can be subsequently loosened to allow the cable to be re-tensioned and re-locked. In another embodiment, for example, a collet member 260, as described below with reference to FIGS. 4-9, may be used as the locking mechanism.

The apparatus 100 may be constructed of various materials. For example, the apparatus 100 may be constructed from metals such as stainless steel or synthetic materials such as plastics, polymers, or composites. In one embodiment, different elements 105, 110, 120 of the apparatus 100 may be constructed from different materials. In one embodiment, the apparatus 100 is disposable. In another embodiment, the elongate shaft 120 may be configured to be reusable by attaching a new crimp body to the elongate shaft 120.

FIGS. 2 and 3 are a side view and cross-sectional side view, respectively, of the apparatus 100 of FIG. 1, but with a washer 103 disposed adjacent the crimp body 105. As described above, the crimp body 105 is configured to engage the hole 53 in the bone 50 to prevent the cable 60 from withdrawing into the hole 53 and thereby holding the tension in the cable 60. According to the embodiment shown in FIGS. 2 and 3, the washer 103 is disposed at the end of the apparatus 100 (i.e., the crimp body 105 is interposed between the washer 103 and neck 110). The washer 103 may further facilitate a proper engagement with the surface of the bone 50 surrounding the opening of the hole 53.

In one embodiment, at least two of the crimp body 105, neck 110, elongate shaft 120, and washer 103 are integrated together to form a one-piece monolithic construction. In one implementation, all four of the crimp body 105, neck 110, elongate shaft 120, and washer 103 are integrated to form a one-piece monolithic construction. In some implementations, for example, the washer 103, crimp body 105, and neck 110 may be formed together as a one-piece monolithic construction that is separately coupled to the elongate shaft 120. In one embodiment, the washer 103 is integrated with the crimp body 105 to form a one-piece monolithic construction with the crimp body 105. In another embodiment, the washer 103 is detachable or detached from the apparatus 100.

In one embodiment, the washer 103 may include one or more pre-embedded cables that can be extended across or through the surface of the bone 50. For example, a first end portion 102A of the pre-embedded cable may be fixed to the washer 103 (e.g. secured within a channel formed in the washer 103 and a second portion 102B of the cable may be wrapped around the bone (e.g., in a cerclage configuration) and/or extended through the hole in the bone. With the second portion 102B of the cable wrapped around and/or extend through the bone, the second portion 102B of the cable can then be inserted through the central passage 140 of the apparatus 100 to be crimped, cut, and tensioned. In one embodiment, the pre-embedded cable 102 extends from an outer edge of the washer 103. The pre-embedded cable may be used to wrap around tissue (e.g., cerclage configuration) to facilitate the reduction and fixation of a fracture. In another embodiment, the channel(s) of the washer 103 may pass-through the entire washer, thus allowing one or more cables to pass through the washer.

According to the embodiment shown in FIG. 3, the central passage 140 has an interior surface 128 that converges in a direction extending from the elongate shaft 120 to the crimp body 105. Such a feature is described in greater detail below with reference to FIGS. 4-9. In one embodiment, locking mechanism elements may extend through the pass-through apertures 122 to engage the cable 60 and lock the cable 60 in place, thereby holding the tension in the cable 60. For example, one or more of the pass-through apertures 122 may have threads that allow one or more set screws or other similar elements to extend transversely into the central passage 140 to securely lock the cable 60 in place.

Figure 4:
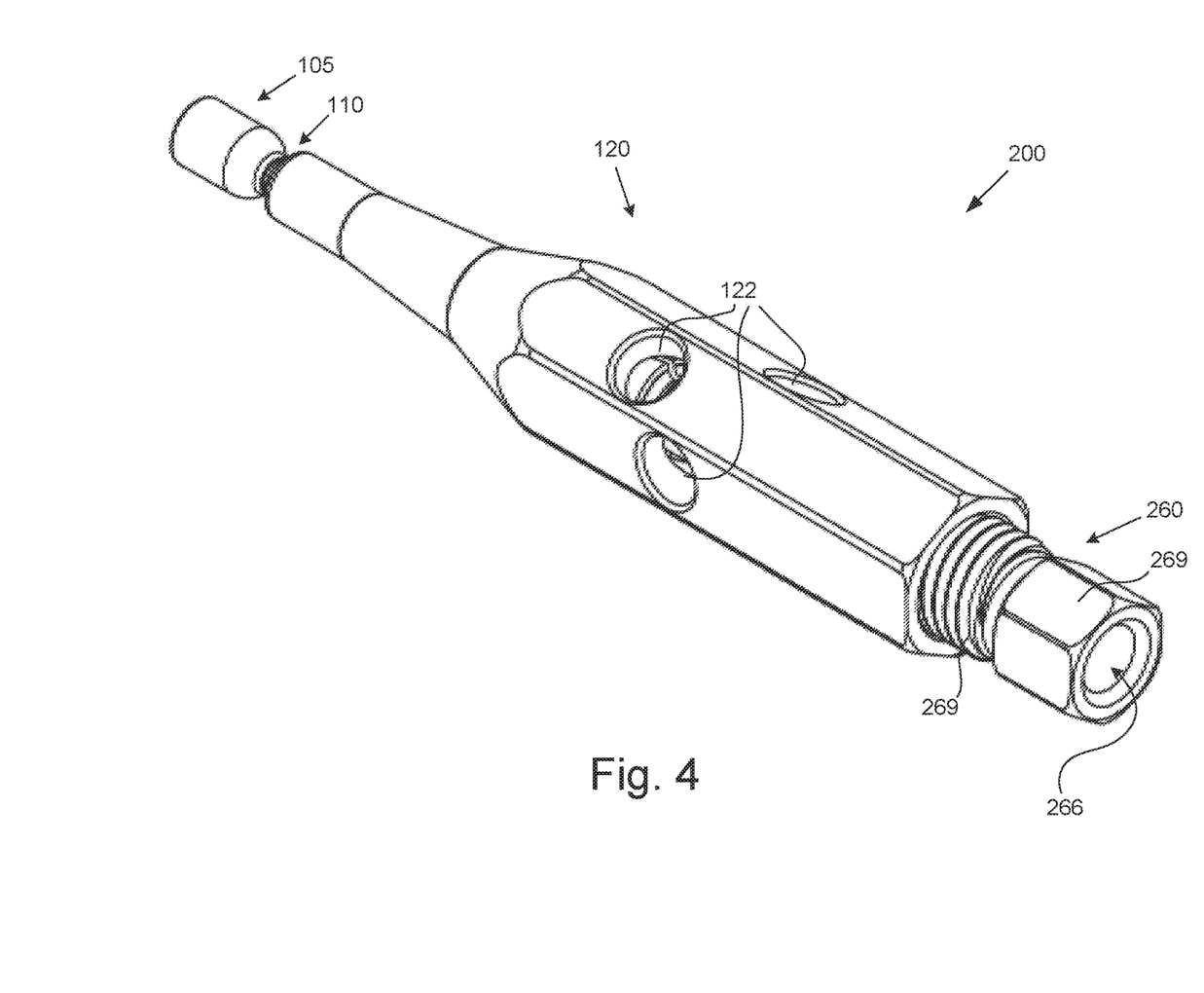
FIG. 4 is a side perspective view of another embodiment of the apparatus, with a collet member partially disposed within a central passage of the elongate shaft.
Figure 5:
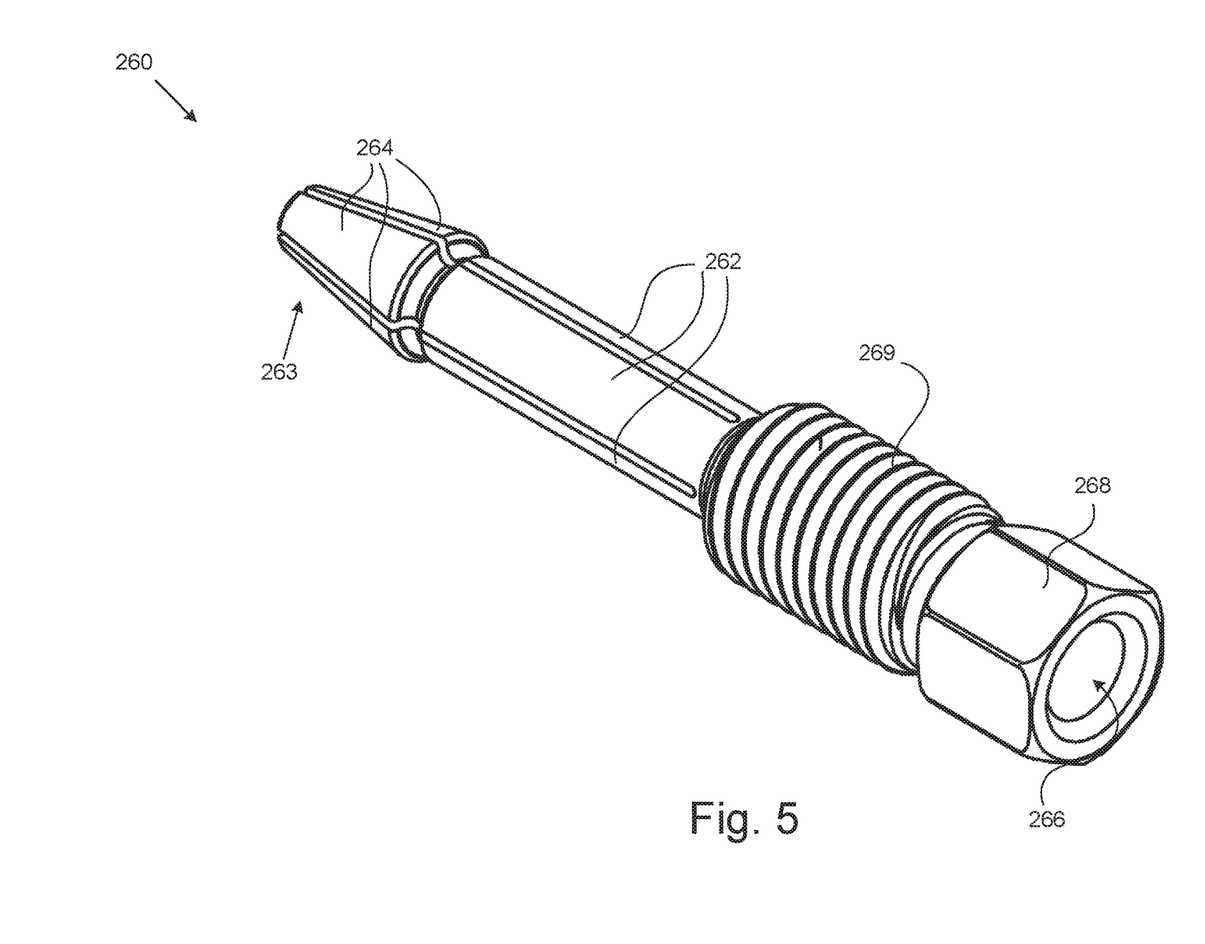
FIG. 5 is a side perspective view of the collet member, according to one embodiment.
Figure 6:
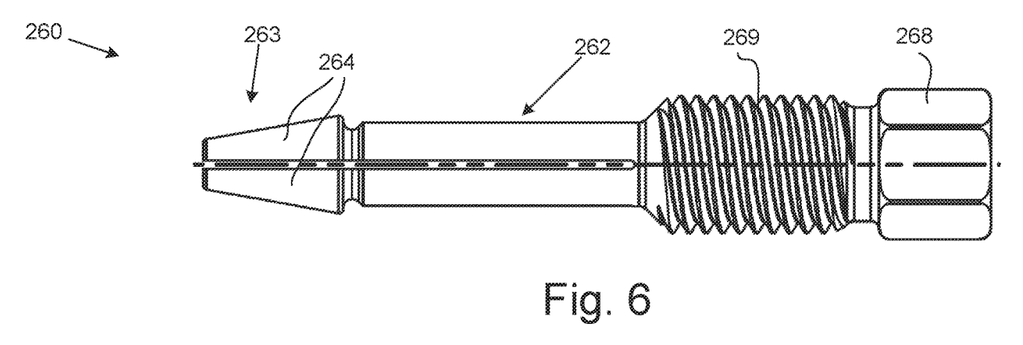
FIG. 6 is a side view of the collet member of FIG. 5, according to one embodiment.
Figure 7:
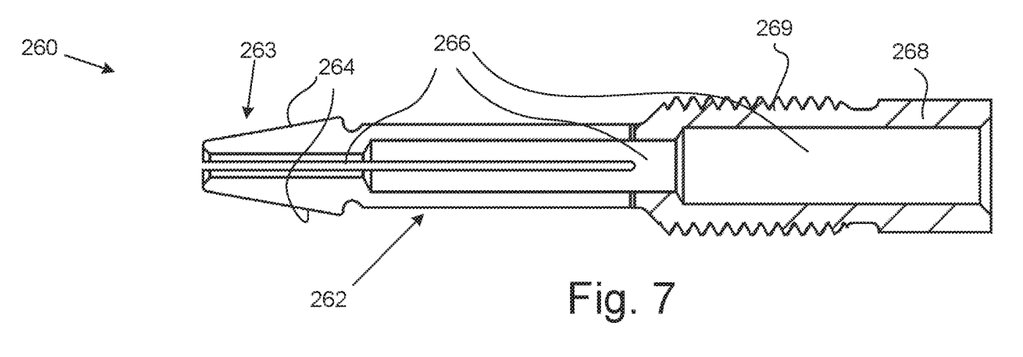
FIG. 7 is a cross-sectional side view of the collet member of FIG. 6, according to one embodiment.
Figure 8:
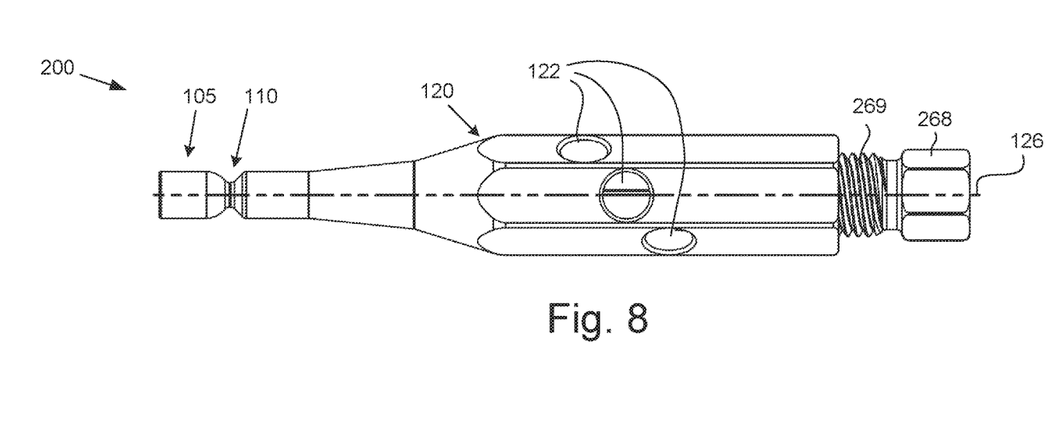
FIG. 8 is a side view of the apparatus of FIG. 4, according to one embodiment.

FIG. 4 is a side perspective view of another embodiment of the apparatus 200 with a collet member 260 partially disposed within the central passage 140 of the elongate shaft 120. FIGS. 5-7 show a side perspective view, a side view, and a cross-sectional side view, respectively, of the collet member 260 and FIGS. 8 and 9 show a side view and a cross-sectional side view, respectively, of the apparatus 200 depicted in FIG. 4.

The collet member 260 is a type of locking mechanism that is configured to clamp around the cable 60 to securely maintain the tension in the cable 60. The collet member 260 is translationally movable within the central passage 140 of the elongate shaft 120. The collet member 260 has a central channel 266 extending through a plurality of prongs 262 (FIGS. 5-7), with the central channel 266 being concentric with the central passage 140. The plurality of prongs 262 are configured to engage the interior surface 128 of the central passage 140 of the elongate shaft 120 and compress inwardly towards the central channel 266 to lock the cable 60 positioned in the central channel 266. In other words, relative translational movement along the central axis 126 of the collet member 260 with respect to the elongate shaft 120 causes the plurality of prongs 262 to move into direct contact with the converging interior surface 128 of the central passage 140. As the collet member 260 continues its translational movement, the plurality of prongs 262 are flex inwards by the converging interior surface 128. As the plurality of prongs 262 are flexed inwards towards the central channel 266, through which the cable 60 is extending, the plurality of prongs 262 clamp around the cable 60 to prevent the cable from slipping or losing tension. With the cable 60 secured, the manually applied tension may be relieved or the tensioner device may be detached from the apparatus 200. In another embodiment, the collet member 260 can be moved backwards, thus allowing the plurality of prongs 262 to flex back outwards in order for the cable 60 to be released or re-tensioned.

According to the embodiment depicted in the figures, the collet member has external threads 269 that are threadably engageable with the conforming internal threads 124 disposed in the central passage 140 of the elongate shaft 120. Relative rotation of the collet member 260 with respect to the elongate shaft 120, accomplished via rotational engagement of the conforming threads 269, 124, causes the collet member 260 to translationally move within the central passage 140 of the elongate shaft 120 and thereby apply the clamping force around the cable 60.

The pass-through apertures 122 extending through one or more walls of the elongate shaft 120 in a direction substantially perpendicular to the central axis 126 of the elongate shaft are configured, according to one embodiment, to receive a tool (e.g., transverse shaft) for inducing relative rotation between the elongate shaft 120 and the collet member 260. In another embodiment, the pass-through apertures 122 include secondary locking features that facilitate and improve the security of the clamping force of the collet member 260 around the cable 60. For example, one or more set screws may be threaded through the pass-through apertures 122 to engage the collet member 260, thus preventing the collet member 260 from inadvertently sliding away from the converging interior surface 128 and thereby preventing the plurality of prongs 262 from losing a secure clamp around the cable 60.

As shown in the figures and according to one embodiment, the collet member 260 has a proximal-end portion 268 that has a non-circular outer periphery. The non-circular outer periphery of the proximal-end portion is mateable with a rotational tool (e.g., a drill or a wrench) for inducing relative rotation between the elongate shaft 120 and the collet member 260.

Figure 10:
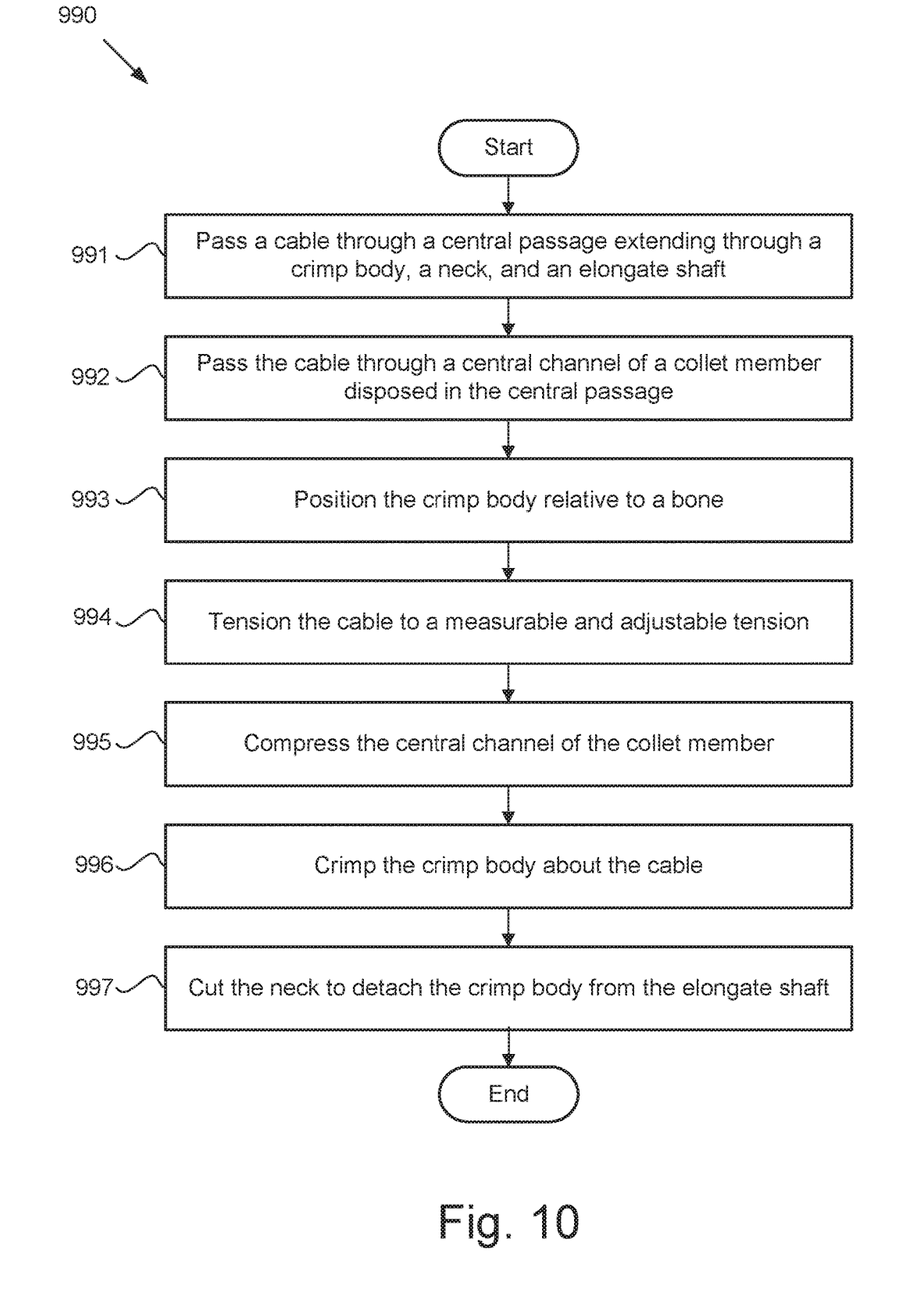
FIG. 10 is a schematic flowchart diagram of a method for attaching the crimp body to the cable, according to one embodiment.

FIG. 10 is a schematic flowchart diagram of one embodiment of a method 990 for attaching the crimp body 105 to the cable 60. The method 990 includes passing the cable 60 through the central passage 140 that continuously extends through the crimp body 105, the elongate shaft 120, and the neck 110 at 991. Optionally, the method 990 further includes passing the cable 60 through the central channel 266 of the collet member 260 disposed within and concentric with the central passage 140 of the elongate shaft 120 at 992. Still further, the method 990 includes positioning the crimp body 105 in a desired position relative to the pre-formed hole 53 in the bone 50 at 993. Because the crimp body 105 is non-movably coupled with the elongate shaft 120, the crimp body 105 can be positioned in the desired position relative to the pre-formed hole 53 by moving or positioning the elongate shaft 120. At such a step in the method 990, the cable 60 is extending from the hole 53 and into the central passage 140. The method 990 further includes tensioning the cable 60 to a measurable and adjustable tension at 994, to cause a measurable and adjustable compression of the bone by the cable in some implementations, and, optionally, compressing the central channel 266 of the collet member 260 to lock the cable 60 at the measurable and adjustable tension at 995. Before the central channel 266 is compressed, the crimp body 105 is positioned in the desired position.

The method 990 further includes crimping the crimp body 105 about the cable 60 at 996 and then cutting the neck 110 to detach the crimp body 105 from the elongate shaft 120 at 997. In some implementations, the hole 53 extends through two bone segments of a fractured bone such that tensioning the cable 60 to a measurable and adjustable tension, and crimping the cable 60, in this manner causes the two bone segments to compress together with a measurable and adjustable compression. Moreover, because the cable 60 passes through the bone, as opposed to around the bone, the compression of the two bone segments is applied in one direction (e.g., unidirectionally) concentric with the cable 60, to more uniformly and evenly distribute the compressive load to the bone segments, as opposed to multiple directions when compression is applied by a cable passing around the bone.

As mentioned above, crimping the crimp body 105 and cutting the neck 110 can be performed in a single action by actuating a dual-purpose crimping/cutting tool 270. In one embodiment, cutting the neck 110 at step 997 includes concurrently cutting the cable 60 positioned within the central passage 140 of the neck 110. In one embodiment, the method 990 may optionally include, after the cable is tensioned to a measurable and adjustable tension, releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus for securing a cable through or around bone, the apparatus comprising:
   a crimp body;
   an elongate shaft;
   a neck coupling and interposed between the crimp body and the elongate shaft; and
   a central passage extending through the crimp body, neck, and elongate shaft, the central passage sized to receive the cable; and,
   wherein:
      the crimp body, the elongate shaft, and the neck are integrated together to form a one-piece monolithic construction; and
      a maximum cross-sectional dimension of the crimp body is larger than a maximum cross-sectional dimension of the neck.

2. The apparatus of claim 1, wherein the central passage is continuous through the crimp body, elongate shaft, and neck such that the cable is concurrently positionable within the crimp body, elongate shaft, and neck via the central passage.

3. The apparatus of claim 2, wherein when the cable is positioned in the central passage within the crimp body, the crimp body is collapsible about the cable to crimp the cable.

4. The apparatus of claim 1, wherein:
   a locking mechanism is disposed within the central passage of the elongate shaft; and
   the locking mechanism is configured to lock a cable extending through the central passage.

5. The apparatus of claim 4, wherein:
   the locking mechanism comprises a collet member translationally movable within the central passage of the elongate shaft;
   the collet member comprises a central channel extending through a plurality of prongs concentric with the central passage; and
   the plurality of prongs of the collet member are configured to engage an interior surface of the central passage of the elongate shaft and compress inwardly towards the central channel to lock a cable positioned in the central channel as the collet member translationally moves within the central passage of the elongate shaft.

6. The apparatus of claim 5, wherein the plurality of prongs of the collet member and the interior surface of the central passage of the elongate shaft converge in a direction extending from the elongate shaft to the crimp body.

7. The apparatus of claim 5, wherein:
   the collet member comprises external threads threadably engageable with conforming internal threads disposed in the central passage of the elongate shaft; and relative rotation between the collet member and the elongate shaft causes the collet member to translationally move within the central passage of the elongate shaft.

8. The apparatus of claim 7, wherein:

the elongate shaft comprises one or more pass-through apertures extending through one or more walls of the elongate shaft in a direction substantially perpendicular to a central axis of the elongate shaft; and the one or more pass-through apertures are configured to receive a tool for inducing relative rotation between the elongate shaft and the collet member.

9. The apparatus of claim 7, wherein:

the collet member comprises a proximal-end portion having a non-circular outer periphery; and the non-circular outer periphery is mateable with a rotational tool for inducing relative rotation between the elongate shaft and the collet member.

10. The apparatus of claim 1, wherein a maximum cross-sectional dimension of the elongate shaft is larger than the maximum cross-sectional dimension of the crimp body.

11. The apparatus of claim 1, further comprising a washer coupled to the crimp body, wherein the crimp body is interposed between the washer and the neck.

12. The apparatus of claim 11, wherein the washer, the crimp body, the neck, and the elongate shaft are integrated together to form a one-piece monolithic construction.

13. The apparatus of claim 11, wherein the washer comprises a pre-attached cable.

14. An apparatus for securing a tensioned cable through or around bone, the apparatus comprising:

a crimp body collapsible about a cable to crimp the cable;

an elongate shaft;

a neck coupling and interposed between the crimp body and the elongate shaft; and a central passage extending continuously through the crimp body, neck, and elongate shaft, the central passage sized to receive the cable such that the cable is concurrently positionable within the crimp body, elongate shaft, and neck via the central passage, the central passage comprising internal threads;

a collet member disposed within and translationally movable within the central passage of the elongate shaft configured to lock the cable extending through the central passage at a measurable and adjustable tension, the collet member comprising external threads threadably conforming and engageable with the internal threads disposed in the central passage of the elongate shaft, and wherein:

the crimp body, the elongate shaft, and the neck are integrated to form a one-piece monolithic construction;

a maximum cross-sectional dimension of the crimp body is larger than a maximum cross-sectional dimension of the neck;

the collet member comprises a central channel extending through a plurality of prongs concentric with the central passage; and the plurality of prongs of the collet member are configured to engage an interior surface of the central passage of the elongate shaft and compress inwardly towards the central channel to lock a cable positioned in the central channel as the collet member translationally moves within the central passage of the elongate shaft.

\* \* \* \* \*